United States Patent [19]
Lauritzen

[11] Patent Number: 5,620,742
[45] Date of Patent: *Apr. 15, 1997

[54] METHOD FOR MAKING ABSORBENT ARTICLES HAVING PRINTED POLYMER COATINGS

[75] Inventor: Nels J. Lauritzen, Piscataway, N.J.

[73] Assignee: McNeil-PPC, Inc., Skillman, N.J.

[ * ] Notice: The term of this patent shall not extend beyond the expiration date of Pat. No. 5,417,789.

[21] Appl. No.: 404,777

[22] Filed: Mar. 15, 1995

Related U.S. Application Data

[62] Division of Ser. No. 272,968, Jul. 11, 1994, Pat. No. 5,454,801, which is a continuation of Ser. No. 959,196, Oct. 9, 1992, abandoned.

[51] Int. Cl.$^6$ .............................. B05D 1/28; B05D 5/00; B05D 3/02
[52] U.S. Cl. ..................... 427/209; 427/256; 427/288; 427/379; 427/428
[58] Field of Search ........................ 427/256, 332, 427/336, 359, 371, 394, 288, 428, 381, 209–211, 379; 604/359, 367, 369, 378, 385.1, 381, 383; 428/195, 282, 286

[56] References Cited

U.S. PATENT DOCUMENTS

| | | | |
|---|---|---|---|
| 2,242,380 | 12/1941 | Courtoy | 427/366 |
| 2,690,415 | 9/1954 | Shuler | 167/84 |
| 3,471,428 | 10/1969 | Hodgeson, Jr. | 260/23 |
| 3,622,423 | 11/1971 | Hadley | 156/309 |
| 3,654,020 | 4/1972 | Robinson | 156/291 |
| 3,666,594 | 5/1972 | Condon et al. | 156/291 |
| 3,814,101 | 6/1974 | Kozak | 128/287 |
| 3,886,941 | 6/1975 | Duane et al. | 128/287 |
| 3,901,240 | 8/1975 | Hoey | 604/364 |
| 3,950,198 | 4/1976 | Cannon et al. | 156/79 |
| 3,994,299 | 11/1976 | Karami | 128/287 |
| 3,995,636 | 12/1976 | Murray et al. | 128/285 |
| 4,014,341 | 3/1977 | Karami | 128/287 |
| 4,041,197 | 8/1977 | Gagné | 427/278 |
| 4,054,141 | 10/1977 | Schwaiger et al. | 604/366 |
| 4,067,182 | 1/1978 | DesMarais | 57/411 |
| 4,100,276 | 7/1978 | DesMarais | 514/24 |
| 4,122,218 | 10/1978 | Bostrum et al. | 427/209 |
| 4,144,371 | 3/1979 | Okie et al. | 428/255 |
| 4,184,902 | 1/1980 | Karami | 156/85 |
| 4,233,345 | 11/1980 | Elias | 427/325 |
| 4,324,246 | 4/1982 | Mullane et al. | 128/287 |
| 4,324,247 | 4/1982 | Aziz | 128/287 |
| 4,333,465 | 6/1982 | Wiegner | 128/290 R |
| 4,355,066 | 10/1982 | Newman | 428/198 |
| 4,360,021 | 11/1982 | Stima | 604/365 |
| 4,522,863 | 6/1985 | Keck et al. | 428/196 |
| 4,585,499 | 4/1986 | Karami | 604/378 |
| 4,590,114 | 5/1986 | Holtman | 428/171 |
| 4,622,036 | 11/1986 | Goodrum | 604/367 |
| 4,629,457 | 12/1986 | Ness | 604/382 |
| 4,676,784 | 6/1987 | Erdman et al. | 604/368 |
| 4,690,679 | 9/1987 | Mattingly, III et al. | 604/383 |
| 4,726,976 | 2/1988 | Karami et al. | 428/137 |
| 4,774,107 | 9/1988 | von Kwiatkowski et al. | 427/211 |
| 4,794,020 | 12/1988 | Lussi et al. | 427/195 |
| 4,826,497 | 5/1989 | Marcus et al. | 604/359 |
| 4,950,500 | 8/1990 | Kauffman et al. | 427/197 |
| 4,976,890 | 12/1990 | Felter et al. | 252/511 |
| 5,098,775 | 3/1992 | Harada et al. | 428/281 |
| 5,417,789 | 5/1995 | Lauritzer | 156/220 |

FOREIGN PATENT DOCUMENTS 0343850 11/1989 European Pat. Off. .
0389023 3/1990 European Pat. Off. .
0389015 9/1990 European Pat. Off. .

Primary Examiner—Shrive Beck
Assistant Examiner—Fred J. Parker

[57] ABSTRACT

This invention relates to polymer film or foam coatings for the covers of absorbent articles. More particularly, this invention relates to absorbent products and processes for making in situ foamed polymer coatings which give an opaque, soft, dry and clean-appearing water-permeable cover to absorbent products such as sanitary napkins, diapers and the like.

8 Claims, 3 Drawing Sheets

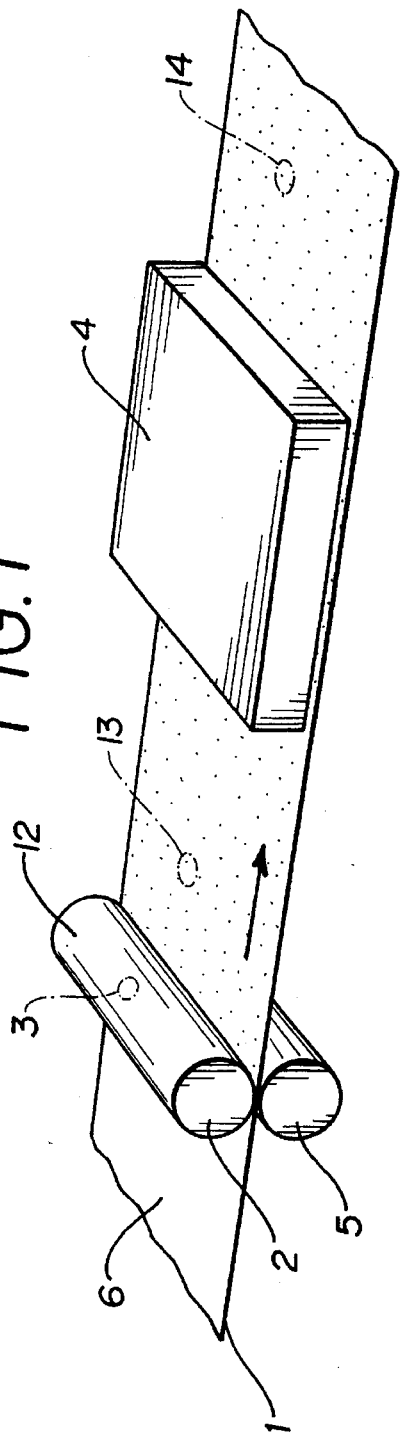
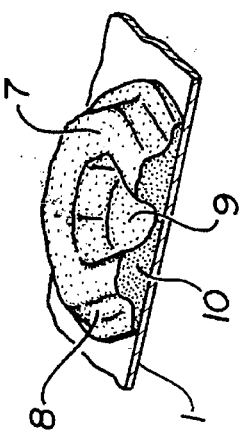
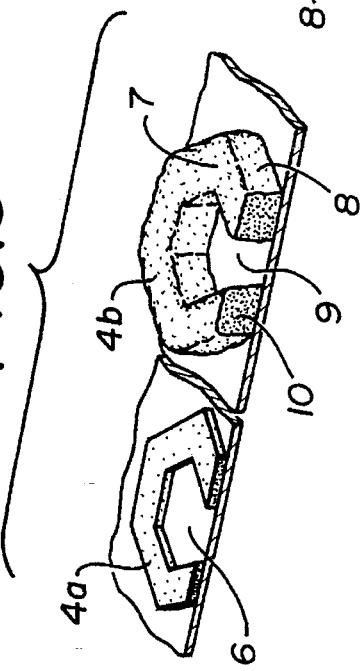
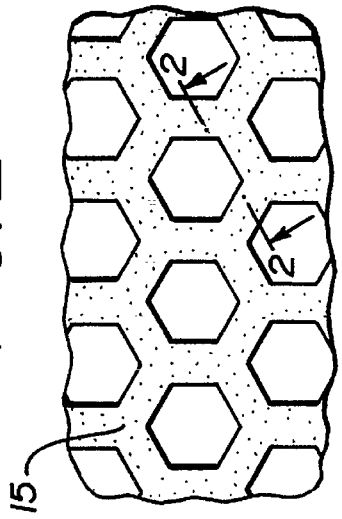

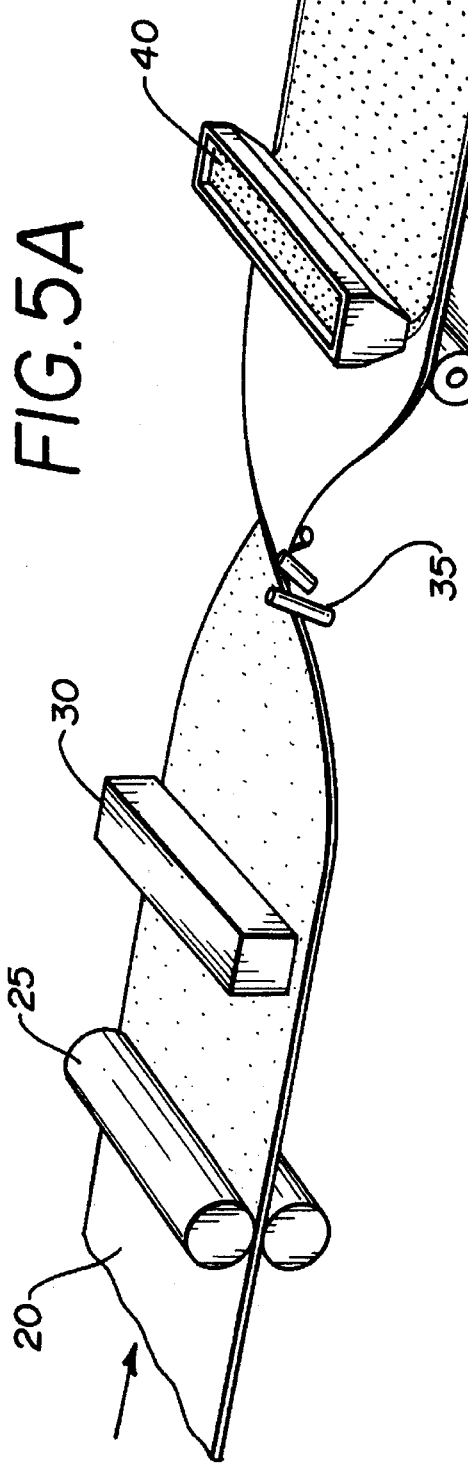
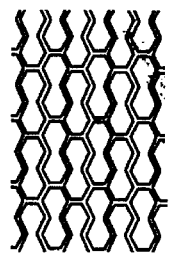
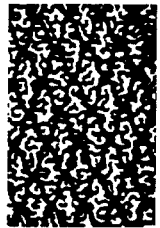
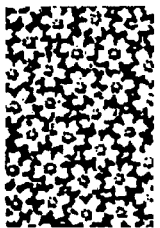

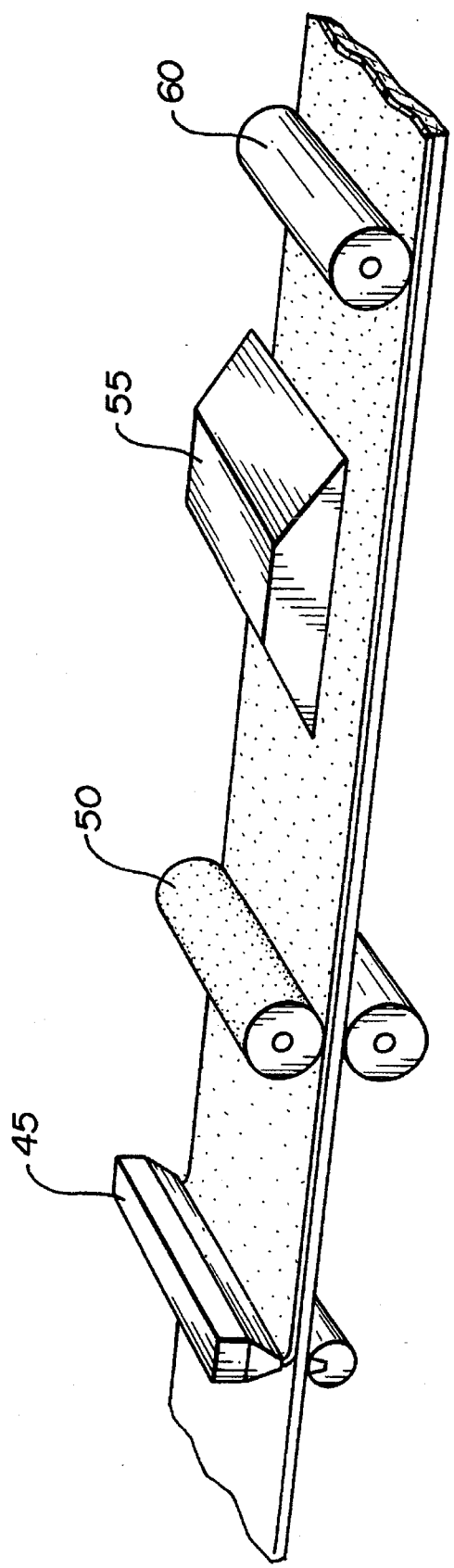

METHOD FOR MAKING ABSORBENT ARTICLES HAVING PRINTED POLYMER COATINGS

This is a division of application Ser. No. 08/272,968, filed Jul. 11, 1994, now U.S. Pat. No. 5,454,801, which is a continuation of application Ser. No. 07/959,196, filed Oct. 9, 1992, abandoned, all of which are hereby incorporated by reference.

This invention relates to polymer film coatings for absorbent articles and more particularly to in situ foamed polymer coatings which give an opaque, soft, dry and clean appearing water-permeable cover to absorbent products such as sanitary napkins, underpads, tampons, diapers and the top sheet construction thereof.

DESCRIPTION OF THE PRIOR ART

Absorbent products such as sanitary napkins and the like are generally constructed to include an absorbent core located with a top or outer cover of water-permeable material. Many absorbent products contain a garment-facing barrier layer composed of a water impervious film material. The absorbent material usually also contains a body-facing cover made of woven or non-woven fabric which prevents the absorbent core from sloughing off or disintegrating during use. In recent years, many products have contained cover material made of two- or three-dimensional apertured polymeric film. These films permit fluid to flow into the absorbent core material without being absorbed into the cover fabric itself. Should fluid be absorbed in the cover fabric, the cover is aesthetically unpleasing to the wearer. The apertured polymeric film materials give the absorbent a clean and dry appearance.

U.S. Pat. No. 4,585,449 (Karami) describes a disposable absorbent product having a water impervious lower layer, an absorbent pad and a top hydrophobic sheet containing surfactant to improve fluid penetration. U.S. Pat. No. 4,622,036 (Goodrum) describes an absorbent structure having a top sheet that is a liquid-permeable material formed from particles of non-dissolvable polymeric material partially fused together to form a continuous sheet.

Another example of such a clean, dry cover made with a hydrophobic material is set forth in U.S. Pat. No. 4,629,457. This patent describes an absorbent facing having "one-way valve" characteristics for aqueous fluid. The one-way valve characteristics are produced by superimposing a thin polymer film and a first web comprising absorbent fibers to form a second web, heating the second web to a temperature such that the polymer is in a formable state, and simultaneously applying shearing and compressive forces to the second web to form the polymer into a coating on the first web. The coating has a fine pattern of continuous areas which lie between and interconnect discontinuous layers.

The use of polymer foams in the manufacture of absorbent products such as sanitary napkins and diapers has been heretofore known. For example, U.S. Pat. No. 3,901,240 (Hoey) describes a laminate containing a crushed, polymeric foam, bonded to non-woven and absorbent layers of an absorbent article. U.S. Pat. No. 4,067,832 (DesMarais) describes flexible polyurethane foam useful as absorbent materials. U.S. Pat. No. 4,100,276 (DesMarais) describes a stable, resilient, polyester foam useful in catamenial tampons.

Thermoplastic materials such as thermoplastic particles, films or fibers have been used in making absorbent products. U.S. Pat. No. 4,054,141 (Schwaiger et al.), U.S. Pat. No. 4,233,345, U.S. Pat. No. 4,360,021 (Stima), U.S. Pat. No. 4,590,114 and U.S. Pat. No. 4,184,902 (Karami) are exemplary of such absorbent products.

Many women find hydrophobic apertured polymer films to be uncomfortable and irritating in comparison with fabric covers. This invention is directed to improvements in the outer surface coatings which contact the human body and may be applied directly to the absorbent core or to woven or non-woven fabrics covering the absorbent core.

Pending U.S. patent application Ser. No. 07/684,629 relates to a process for making a low cost absorbent pad through the use of low cost manufacturing techniques including a continuous production technique in which all necessary raw material components are incorporated in a stepwise fashion and are bound together in a unitary design not employing adhesive. During the course of this method, a polymer cover formulation is applied in a pattern to a nonwoven web.

SUMMARY OF THE INVENTION

In accordance with this invention, absorbent products are made with a patterned film of polymeric material which has been formed on woven or nonwoven fabric material covering a substrate of absorbent material. According to one embodiment of the method of this invention, a polymer material is deposited on the woven or nonwoven web with an etched print roll in a geometric pattern determined by the roll etching. Alternatively, a geometric pattern of polymer may be obtained by using a patterned print screen. Screen printing is especially useful in when a heavy addition of polymer is desired.

Preferably, the polymer contains one or more blowing agents which cause the polymer to expand or foam in situ to approximately 5 to 10 times the original volume of polymer prior to or during curing. The foam is then cured by crosslinking the foamed polymer into an opaque, outwardly extending, mounded, knobby, non-reticulated, repeating pattern of geometric shapes or units which are bonded to one another and to the substrate such that the vertical portion of the geometric shape extending from the substrate surface is about 5 to about 10 times the original polymer height. Curing may be accomplished by any means known to those of skill in the art. For example, radiant energy such as heat, ultraviolet light or electron beam or the like may be used.

The resulting coating has a clean appearance in use, with the upper portion of the vertical geometric shapes remaining clean and dry in a moist environment due to their hydrophobic characteristics. The pattern is designed in such a way that some areas of the substrate are free of polymer or may be coated with thin layers of hydrophilic polymer such that body fluids can pass through the cover into the absorbent core. The resulting cover maintains its clean appearance and dry feeling even after body fluids flow through it because the body fluid will be repelled by the hydrophobic polymer material. Advantageously, however, the substrate on which the hydrophobic polymer is deposited is a fabric material and more acceptable to the touch to many women.

In another embodiment of this invention is a low-cost panty shield-type product with a cover made in accordance with the foregoing process, i.e., forming the cover in situ, as well as forming a barrier layer in situ. A low cost, stabilized fibrous web can be printed with polymer material and cured. The web can then be turned over such that the printed side faces down, away from the side from which the printing roll is located, and an in situ polymer barrier layer can be extruded onto the side opposite that already printed. Prior to extruding the barrier layer, additional active elements such as superabsorbent particles or odor control agents may be incorporated into the web.

BRIEF DESCRIPTION OF THE DRAWINGS

FIG. 1 is a perspective view of a roll-over-roll etched printing station used to apply polymer to a substrate moving through the rolls to a curing station which sets or hardens the polymer.

FIG. 2 is a partial sectional plan view of the etched geometric configuration of the roll and the resulting polymer coated substrate.

FIG. 3 is a view taken above the plane 2—2 in FIG. 2 after passing through the curing station.

FIG. 4 is a view of a polymer foam coated on a substrate similar to FIG. 3, using the same printing roll shown in FIG. 2 which polymer foam is allowed to collapse somewhat during curing to fill the valley with polymer foam and completely coat the underlying substrate.

FIGS. 5A and 5B are perspective views of apparatus used in making a panty shield having a printed cover and extruded barrier.

FIG. 6 shows three preferred patterns for the polymer to be printed onto the cover of the products of this invention.

DETAILED DESCRIPTION OF THE PREFERRED EMBODIMENTS

With reference to the accompanying drawings, in FIG. 1 there is a non-woven fibrous substrate 1 which is continuously passed between an etching roll 2 and support roll 5. Polymer is coated onto the etching roll surface 12 using a die or hopper (not shown) and deposited on substrate 1 as the roll turns and contacts substrate surface 6. The coated substrate surface 1 continues moving in the direction of the arrow to a curing station 4 where the polymer is cured. The curing step may be accomplished by means of radiant or thermal energy, e.g., heat, ultraviolet light, electron-beam or other means known to those of skill in the art. The possible shapes of the set geometric units of polymer at position 14 are shown in FIGS. 3 and 4.

The polymer may, optionally, contain blowing agents, which cause the polymer to expand just before and/or during curing to develop the final foamed geometric shapes 4b and 8 shown in FIGS. 3 and 4. In the cases in which foaming is not employed the cured polymer resembles the solid geometric shape shown in FIG. 3 as 4a. FIG. 2 is a plan view of a portion of the surface of print roll 2 at position 3 and also a plan view of a portion of the surface of the polymer 15 applied to surface 6 of substrate 1 at position 13.

Closer inspection of the Figures will indicate that the foamed and set polymer 4b of FIG. 3 and 8 of FIG. 4 has a mounded shape that is somewhat wider at the base of the pattern where the polymer contacts the substrate than at the substrate top surface 7. Top surface 7 and vertically extending side walls 8 of the cured foamed polymer in FIGS. 3 and 4 have a "knobby" surface. The "knobs" are achieved by the formation of small bubbles or foam during the outgassing stage of the curing process. The bubbles are stabilized in the curing process and the "knobby" appearance is thereby achieved. The geometrically formed units 4a, 4b and 8 are firmly adhered to each other as is shown in FIG. 2 and firmly adhered to substrate surface 6 of FIG. 1.

Turning to FIG. 3, there are open areas 9, provided for the transfer of body fluid through the substrate to a core of absorbent material. The polymeric pattern thus gives the appearance of an apertured polymeric "clean, dry" facing. However, the facing-material is a fabric, thus adding to the comfort of the wearer.

Substrate 6 may be a woven fabric or a nonwoven stabilized web of fiber, laid in a random orientation with no preformed apertures. The substrate can be hydrophilic or hydrophobic or have intermediate characteristics produced by mixing hydrophilic and hydrophobic fibers such as rayon and nylon or the like. The characteristics of the fibers may also be modified by the addition of surfactants to render the fibers more hydrophilic. A hydrophobic, apertured, nonwoven web having a repeating geometric pattern of openings designed to pass fluid is useful as a substrate in the products of this invention. The substrate can also be a film if desired, or a pad of absorbent material.

The polymer should be applied to the substrate and allowed to partially or totally saturate or coat the substrate to insure a solid bond upon curing.

The polymer can be applied as a plastisol or organosol or otherwise, such as a solid, to the fiber substrate. The polymer may then be cured or foamed prior to curing. The polymer may be foamed by employing a blowing agent. The blowing agent expands and evaporates, leaving a grossly-increased volume of polymer, preferably about 5 to about 10 times the volume of unfoamed polymer.

Prior to foaming, the polymer is placed on a fabric, film or fibrous web substrate in a uniform, repeating, geometric design which on foaming and curing results in a cover material which is flexible, resistant to wear, soft to the skin and mucosa and dry to the touch in moist environments. The polymer may be applied to the substrate of means of printing, coating, etching, silk screening, or any other method known to those of skill in the art.

The polymer can be any hydrophilic or hydrophobic polymer which can be formed into a geometric design, particularly a polymer which can be foamed and solidified to produce a geometric shape having a vertical height between at least about 5 and about 10 times the height of unfoamed polymer. Most preferably, the height should be equal to or greater than the width of the area of the vertical plane 10 in FIGS. 3 and 4 of the geometric foamed polymer taken at a point one-half of the vertical height of the wall of the foamed polymer.

Referring to FIG. 5A, a low cost, stabilized, fibrous web 20, such as Scotts High Loft SPP (available from Scott Paper Company of Philadelphia, Pa.) is brought through a rotary screen printing station 25. At the printing station, the in situ cover is pattern-applied. The rotary screen is used to apply a relatively heavy amount of polymer, between about 0.4 oz./yd. to about 1.2 oz./yd. The pattern should be aesthetically pleasing (FIG. 6A), can aid in pad placement (FIG. 6B), and or can be effective in providing surface channels and reservoirs to aid in fluid management (FIG. 6C). The polymer cover is heat-cured as it passes through an infrared tunnel 30. The cured cover serves to improve the structural integrity of the web. The web is then turned over by inverting bars 35 in order to present the underlying surface, which will become the garment-facing side of the product, to be processed.

Optionally, particulate or other types of materials may be added to the now-exposed side of the web at this point in the process. As depicted in FIG. 5A, particulate material, such as superabsorbent, may be added to the web using a hopper 40 or any other apparatus known to those of skill in the art.

Referring now to FIG. 5B, the in situ barrier may be applied by direct extrusion 45 onto the web. The extruder delivers a hydrophobic barrier such as polyethylene directly to the surface of the web. The barrier material should be compatible with the material in the web in order to insure that the barrier and web are adequately adhered to one another. After extrusion onto the web, the barrier may be "texturized" or imparted with a pattern in order to reduce plastic noise and feel. The barrier may also be cured, if necessary.

A placement adhesive may be placed on the barrier using a roll print process 50 which distributes the adhesive in a controlled pattern. The printed adhesive may then be crosslinked and cured using an ultraviolet curing unit 55. Release paper such as silicone-coated Kraft paper is then applied to the bare adhesive in order to protect the adhesive from dust and dirt. The product can then be die cut at a die cutting station 60.

The polymer used for the printed cover can be a flexible, preferably white, polyurethane foam obtained by reacting an aliphatic diisocyanate and polyether polyol with an admixture of polyfunctional, crosslinking agents, stannous octoate catalyst, inorganic hydroxide strong base catalyst and water such as described in U.S. Pat. No. 4,067,832, which is hereby incorporated herein by reference, or a resilient polyester foam material such as disclosed in U.S. Pat. No. 4,110,276, which is hereby incorporated herein by reference, prepared by reacting an acyl halide, polyol and polyhydroxy crosslinking agents in the presence of an alkali metal carbonate to prepare a flexible, resilient foam. The coating may, alternatively, be a polyester foam as taught in U.S. Pat. No. 4,239,043, which is hereby incorporated herein by reference, or foamed latex or other monomers, polymers and terpolymers as disclosed in U.S. Pat. No. 3,901,240, which is hereby incorporated herein by reference.

Any foamable plastic polymer-which forms a flexible open celled or closed celled foam may be employed in the products and process of this invention. For example, latex foams are most preferable, however other foams such as polyvinyl chloride foams, polystyrene foams, crosslinked polyethylene foams, polypropylene foams, polyurethane foams, polypropylene foams, polyurethane foams, acrylic and methacrylic polymer foams or foamed rubber may be employed. While the foam can be formed by preparing a gasified monomer before curing it is much preferred to employ monomer compatible blowing agents known to those of skill in the art such as air, carbon dioxide, volatile alkanes such a 2-methyl propane, volatile halo alkanes such as methyl chloride, dichloromethane and the like, volatile alcohols and ethers and various halocarbons including fluorocarbons.

Preferably the process of this invention entails forming the polymer of choice into a fluid polymer phase and bringing that fluid polymer phase to a low density cellular state. This low density cellular state should be preserved by setting the polymer into a flexible, resilient, soft, foamed coating. This is accomplished by creating small discontinuities or cells in the plastic phase, causing the cells to grow to the desired five fold or preferably ten fold increase in volume from unfoamed polymer. The cellular structure should then be stabilized by physical or chemical means. Preferably, the pressure inside the cell that causes the polymer to foam is generated by the blowing agent dispersed or dissolved in the polymer mixture. For example, a fluorocarbon blowing agent can be uniformly dispersed in the polymer. Heating this mixture causes a rapid and controllable expansion of the polymer mixture. Similar expansion can be obtained by reacting compounds in the deposited polymer during curing, to cause evolutions of a gas such as carbon dioxide which causes the polymer to expand. The expanded polymer is then set or solidified by heat or other known means.

Alternatively, the foamable composition may be deposited on the substrate under pressure from a die or an extruder and thereafter expanded at atmospheric or reduced pressure.

Polyethylene and polypropylene foams can be prepared by crosslinking the polyethylene chemically using peroxides or by radiation which is preferred using an electron gun or other means. The expanded polyethylene foam is prepared by mixing polyethylene, a chemical blowing agent and optionally a crosslinking agent at low or medium temperature, shaping the polymer by applying it to the substrate using an engraving, screen or other known depositing process, chemically treating or radiating to polymer to crosslink the polymer and heating the polymer and heating the polymer to expand. The polymer is then cooled to form a solid foamed coating. Polyurethane foams can be prepared from a polyfunctional isocyanate and a hydroxyl-containing polymer along with a catalyst and blowing agent as a halocarbon.

Polystyrene foams can be produced by decompression of polymer as it leaves a die, which is used to coat the engraving roll or silk screen. The engraving roll or silk screen then prints the polymer onto the substrate.

Latex rubber foams can be made by dispersing a gas or solid in a liquid phase, stabilizing the liquid polymer phase and subsequently treating the polymer after its application to the fiber substrate by heat. The heat then causes the gas to expand the rubber to cure. Expanded acrylonitride-butadiene rubber, expanded butyl rubber, expanded natural rubber, expanded neoprene, expanded latex foam, polyethylene, polypropylene, polyurethane, polyvinyl chloride and silicon foams and compatible mixtures thereof, are all useful in forming the geometric foamed coating of this invention.

Most preferably, the polymer material useful in the products of this invention is polyvinyl chloride. Most preferably, it is combined with various plasticizers known to those of skill in the art to form a plastisol. This plastisol is combined further with blowing agents, such as nitrogen or another inert gas and encapsulated carbon dioxide to form a foaming composition. The plastisol is then applied to an etched printing roll which in turn applied the plastisol to a nonwoven substrate made of staple synthetic or natural fibers and/or stabilized paper pulp fibers. The substrate moves under a curing station which directs heat at the plastisol-coated substrate in order to cure the polymer and cause it to foam. The curing temperature and curing time is dependent upon the formulation of the plastisol as well as upon the heat source used during the cure. Using the preferable composition of polyvinyl chloride in a plastisol composition, the formulation should be cured at a temperature of from about 300° F. to about 475° F. for a time period of between about 15 and about 45 seconds.

In one preferred embodiment of the process and products of this invention, a fibrous web material such as Scotts High Loft SPP is brought through a printing station. This web is preferably made up of various blends containing thermoplastic fibers such as Enka bicomponent fiber having a polyester core and a polyethylene sheath, and Dupont Pulplus®, a polyethylene microfiber available from E. I. dupont de Nemours of Wilmington, Del. A preferred plastisol cover formulation contains 50% by weight polyvinyl chloride resin, such as Geon® 180×5 available from B. F. Goodrich and 50% plasticizer such as butyl benzyl phthalate, such as Santicizer 160, available from Monsanto Corporation of St. Louis, Mo. This plastisol cover formulation should be applied to the web in amounts between about 0.4 and about 1.2 ounces/yd$^2$.

The polymer film or foam covers of this invention are particularly useful for their appearance and comfort. Not only are the coatings soft, flexible and compressive, they offer a clean, fresh appearance and provide an easy means of controlling moisture transfer to the absorbent areas of diapers, sanitary napkins, tampons and the like. The flexible and compressive urethanes, vinyl, latex, foam rubber and olefin foams are particularly useful for comfort and cushioning.

The film or foam coating of this invention can be whitened to improve its appearance and enhance its stain-masking characteristics by incorporating in the polymer mix prior to transfer to the substrate, various pigments such as clays, calcium carbonate, talc, titanium dioxide and the like. The addition of white pigment is particularly useful for the absorbent articles of this invention in improving the appearance, both before and after use, of the article. The coated foamed surface of the absorbent article has a clean, white appearance which is very desirable and is a preferred embodiment of the products of this invention.

The surface geometry of this invention is controlled by the plastisol or foamed plastisol while the white appearance is due to the high opacity of the foamed polymer and preferably by the addition of white pigment. The foamed plastisol allows the formation of an infinitely variable variety of designs of porous film in situ on fiber substrates. The degree of moisture penetration is easily controlled by the geometric design, the hydrophobic-hydrophilic characteristics of the foam and by the physical properties of the polymer as its is expanded and then cured. Less sharply defined, geometric patterns are also possible to create by modifying the polymer viscosity or cure time. This causes the sharply defined printed shape to slump. The shape can then cover all or a portion of the underlying substrate.

A particular advantage of the foamed in situ process of this invention, however, is to produce rather sharply defined geometric designs of white surfaces which have high vertical walls extending from the fabric substrate which insures that the upper surface of such walls remains dry while fluid is passed through uncovered or lightly covered areas of the substrate in the valleys between the vertical walls of the geometric design and then into the absorbent core.

The in situ foam covers of this invention are an extremely cost effective way of manufacturing foam covered absorbent products. The foamed geometric design increases the cover's working surface and allows further control of the cover's absorption properties as well as improving the appearance of the surface. The foamed polymer film also forms surface channels, which encourage vertical fluid penetration into the absorbent core of pads. This maintains dry upper surfaces and discourages side failures.

The foam cover of this invention is also an excellent method by which to combine a cover film and absorbent fiber in a hybrid structure. The method of this invention strengthens the fiber web by coating the surface fibers and interstices with film or foam. Fiber substrate interstices therefore do not trap fluids and become stained. The open fiber portions in the valleys created by the pattern pass fluid to the absorbent core while the vertical walls of the foam hide any staining in the valley. The cover, once hybridized with a foamed film, becomes more structurally stable and resists bunching of the surface cover. The foamed cover retains its cured appearance during and after use.

What is claimed is:

1. A process for making an absorbent product comprising applying a fluid polymer coating to a first surface of an absorbent fibrous web in a repeating geometric pattern, curing said polymer coating, applying a fluid polymer coating to a second surface of said web, opposite said first surface, and curing said polymer coating on said second surface to form a fluid-impermeable barrier.

2. A process according to claim 1 further comprising applying adhesive material to an exposed surface of said fluid-impermeable barrier.

3. A process according to claim 1 further comprising cutting said web after forming said fluid-impermeable barrier to form separate absorbent products.

4. The process of claim 1 wherein said polymer coating is applied to said first surface and cured prior to the application and cure of said fluid-impermeable polymer.

5. The process of claim 4 which further comprises inverting said fibrous web after said polymer coating has been cured.

6. A process according to claim 5 further comprising adding particulate matter to said second surface of said web prior to applying the fluid polymer coating.

7. A process according to claim 6 wherein said particulate matter comprises superabsorbent material.

8. A process according to claim 6 wherein said particulate matter comprises odor-control material.

\* \* \* \* \*